United States Patent [19]

Jackisch

[11] 4,423,262

[45] Dec. 27, 1983

[54] PREPARATION OF DIBROMOSTYRENE

[75] Inventor: Philip F. Jackisch, Royal Oak, Mich.

[73] Assignee: Ethyl Corporation, Richmond, Va.

[21] Appl. No.: 130,119

[22] Filed: Mar. 13, 1980

[51] Int. Cl.$^3$ ............................................. C07C 17/34
[52] U.S. Cl. .................................................. 570/193
[58] Field of Search ..................... 260/650 R; 570/193

[56] References Cited

U.S. PATENT DOCUMENTS

| | | | |
|---|---|---|---|
| 2,290,758 | 7/1942 | Levine et al. ................... | 260/650 R |
| 2,561,516 | 7/1951 | Ladd et al. ...................... | 260/650 R |
| 2,996,554 | 8/1961 | Olah et al. ...................... | 260/650 R |
| 3,065,280 | 11/1962 | Vogt ............................... | 260/654 D |
| 3,204,004 | 8/1965 | Sexton ............................ | 585/436 |
| 3,664,966 | 5/1972 | Gordon ........................... | 260/654 D |
| 3,867,468 | 2/1975 | Vofsi et al. ..................... | 260/650 R |
| 3,896,181 | 7/1975 | Brown et al. .................... | 260/654 D |

OTHER PUBLICATIONS

J. Dockx, Quaternary Ammonium Compounds in Organic Synthesis, pp. 441–456, Aug. 1973.

*Primary Examiner*—Thomas A. Waltz
*Assistant Examiner*—Joseph A. Boska
*Attorney, Agent, or Firm*—Donald L. Johnson; John F. Sieberth; John F. Hunt

[57] ABSTRACT

A process for the preparation of an ar-dibromostyrene which comprises aqueous alcoholic alkali dehydrobromination of 2-bromoethyl dibromobenzene in the presence of a phase transfer catalyst at a temperature of between about 0° C. and about 150° C. The ar-dibromostyrenes have the particular utility as a co-monomer for the preparation of a co-polymer exhibiting a flame retardancy.

7 Claims, No Drawings

4,423,262

PREPARATION OF DIBROMOSTYRENE

BACKGROUND OF THE INVENTION

This invention relates to the dehydrohalogenation of a β-haloethyldibromobenzene. More particularly, this invention relates to the dehydrohalogenation of a β-haloethylhalobenzene in an aqueous alcoholic alkaline medium using a phase transfer catalyst.

DESCRIPTION OF PRIOR ART

Various methods of preparation of dibromostyrene are known. Most involve dehydrobromination of either α-bromoethyldibromobenzene or β-bromoethyldibromobenzene and also the dehydration of the α-hydroxyethyldibromobenzene.

The various methods of dehydration of α-hydroxyethyldibromobenzene include the use of $Al_2O_3$, i.e. passing the α-hydroxyethyldibromobenzene over $Al_2O_3$ at about 280° C. This is reported in Chem. Abstracts by M. M. Koton (1953) as having only a 57 percent yield.

British Pat. No. 986,634 is an application of dehydrobromination to both the α-haloethylbromobenzene and β-haloethylbromobenzene. It describes a method of using $CaSO_4$ as a catalyst. The chosen haloethylbromobenzene is passed over granular calcium sulfate with superheated steam at a temperature of 180° to 350° C. Other catalysts mentioned in the literature are $CaCl_2$ and CaO.

U.S. Pat. No. 3,737,469 describes the preparation of bromostyrene simultaneously with an alkyl bromide. This process is conducted by beginning with either α-bromoethylbromobenzene or β-bromoethylbromobenzene and reacting the selected compound with a molten alkali metal bromide or with an alkaline earth bromide at a temperature between about 250° C. to 500° C. in the presence of an alkanol. The alkanol acts as a scavenger agent picking up liberated HBr, thus favoring the formation of the products.

U.S. Pat. No. 3,867,468 describes a process for the simultaneous production of dibromostyrene and an alkyl bromide by reacting bromoethyldibromobenzene and an alkanol. When beginning with α-bromoethyldibromobenzene, the reactants are contacted with molten alkali metal bromides or alkaline earth metal bromides at 300°–500° C. When beginning with the β-bromoethyldibromobenzene, the reaction temperature suggested is 400°–550° C. to effect a pyrolysis reaction. Here again the alkanol is used as a scavenger to accept the eliminated HBr, termed a "reactive-diluent".

U.S. Pat. No. 3,980,722 also describes a method of producing dibromostyrene simultaneously with an alkyl bromide. This process is conducted by reacting bromoethyl-dibromobenzene with an alkanol at an elevated temperature in the gaseous phase at about 400°–550° C. Another improvement described in this patent is the presence of peroxides or other sources of free radicals to act as a catalyst. Thus, conducting the reaction of the catalyst allows a substantially lower temperature to effect the reaction of about 280° C.

U.S. Pat. No. 3,966,831 describes a method of production of dibromostyrene by reacting β-bromoethyldibromobenzene in the presence of water or alkanol and a free radical source such as a peroxide at a temperature between 280° C. and 470° C.

The use of quaternary salts of Group V-A elements with the formula $(R_1R_2R_3R_4M)^+X^-$ as phase transfer catalysts are described in U.S. Pat. No. 3,992,432. This patent depicts a method of catalyzing a reaction in which the reactants in a heterogeneous medium are located in two distinct or separate phases of differing polarity.

The use of quaternary ammonium halide salt as a phase transfer catalyst in various elimination reactions is suggested in the literature. W. P. Weber and G. W. Gokel, *Phase Transfer Catalysis in Organic Synthesis*, 1977, (p. 125), depict the use of phase transfer catalyst for dehydrohalogenation of alkyl halides and of α-halo-olefins to yield acetylenes. They suggest a phase transfer catalyst such as tetrabutyl ammonium bromide (or bisulfate) to convert 1,2-dibromoethylbenzene to phenylacetylene.

J. Dockx, in *Quaternary Ammonium Compounds in Organic Synthesis*, reports the use of a phase transfer catalyst in the production of styrene from phenethylbromide in 50 percent NaOH.

SUMMARY OF THE PRESENT INVENTION

The present invention provides a process for the production of ar-dibromosytrene via dehydrobromination of a β-bromoethyldibromobenzene by reacting β-bromoethyldibromobenzene with a tertiary alcohol in the presence of a phase transfer catalyst in an alkaline medium.

DESCRIPTION OF PREFERRED EMBODIMENTS

In the process of the present invention β-bromoethyldibromobenzene is contacted with an alkali metal hydroxide, an alkali metal halide, a lower alkyl tertiary alcohol and a phase transfer catalyst to produce ar-dibromostyrene.

The alkali metal hydroxide is used in a concentrated solution of about 20 percent or greater. Sodium hydroxide and potassium hydroxides are preferred. Sodium hydroxide is the most preferred as it is the least expensive. A saturated solution or nearly saturated sodium hydroxide solution, say, 50–60 percent, is the most preferred. Concentration outside these ranges may be employed, though not with good results.

An alkali metal halide, or other source of common ion, is used to saturate the solution and thus force a movement of other reactants toward dissolution in the organic phase. Sodium chloride and potassium chloride are preferred. Sodium chloride (in conjunction with sodium hydroxide as the alkali metal hydroxide) is most preferred as it is readily available in purified form and is also most economical. A quantity sufficient to saturate the alkali metal hydroxide is preferred.

The lower alkyl tertiary alcohol is the source of a strong alkoxide ion and acts as a promoter and catalyst in the dehydrobromination. A lower alkyl tertiary alcohol of about 4 to about 7 carbon atoms is preferred. 2-Hydroxy-2-methylpropane, i.e., tert-butanol, is most preferred due to base strength and ease of removal by water washing after reaction is completed.

The phase transfer catalyst is used in order to favor optimum extraction of the dehydrobromination reagents into the organic phase, particularly to t-butoxide ion formed under the process described in this invention. A tetraalkyl quaternary ammonium halide having 8–17 carbon atoms is suitable. Triethylpentyl ammonium bromide is preferred because of its ability to optimize the solubility of t-butoxide in the organic medium, thus yielding an increase in the rate of elimination.

Other alkyl quaternary ammonium halides may be employed.

The reaction is carried out at a temperature in the range of about 0° C. to about 150° C. and preferably between about 20° C. and about 45° C.

The t-butyl alcohol and triethylamyl ammonium bromide can be used in substantially stoichiometric quantities or present in concentrations of about 0.05 mole to about 10 moles of t-butanol and about 0.001 to about 1.0 moles of triethylamyl ammonium bromide per 1 mole of substrate, β-bromoethyldibromobenzene.

Although NaOH and KOH are preferred, other caustic substances can provide the alkaline medium, and although NaCl and KCl are preferred, any organic or inorganic (salt) compound which will aid in saturation can be employed.

The process of the present invention has the advantage of giving high yields of ar-dibromostyrene as a monomer. It has the added advantage of being conducted at a low temperature while still providing a good yield at a good rate. The ability to be conducted at low temperature also eliminates the need for sudden quenching of the product to prevent polymerization.

This invention also is less costly than methods requiring sodium ethoxide in ethanol or potassium t-butoxide in t-butanol. The ability to proceed at a lower temperature also increases the safety in preparing dibromostyrene.

The following examples are illustrative and not limiting of the process of the present invention.

EXAMPLE 1 ar-Dibromostyrene via Phase Transfer Catalyzed Dehydrobromination

A solution of 147.90 g. (0.431 mole) of 2-bromoethyl-dibromobenzene in 250 ml. of methylene chloride was stirred for 7 ks (2 hours) at 5 Hz (300 rpm) at 313 K. (40° C.) with 150 g (2.25 mole) of 60 percent sodium hydroxide solution and 3.12 g. (0.0124 mole) of triethylpentyl ammonium bromide. The product was washed with three 500-ml portions of water, dried over calcium sulfate (Drierite), and stripped of solvent in a rotary evaporator at a bath temperature of 323 K. (50° C.). The yield of product was 106.97 g. (77.2 percent of theory). GC analysis showed 27.1 percent of the desired ar-dibromostyrene, the remainder being largely unreacted starting material.

EXAMPLE 2

A solution of 168.3 g (0.491 mole) of 2-bromoethyl-dibromobenzene in 200 ml. of methylene chloride was stirred for 7 ks (2 hours) at 5 Hz (300 rpm) at 298 K. (25° C.(with 200 g (2.5 mole) of 50 percent sodium hydroxide solution and 3.10 g (0.0123 mole) of triethylpentyl ammonium bromide. The product was washed with five 500 ml portions of water, dried over calcium sulfate (Drierite), and stripped of solvent in a rotary evaporator at a bath temperature of 323 K. (50° C.). The yield of product was 119.32 g (81.6 percent of theory). GC analysis showed 55.7 percent of the desired ar-dibromostyrene, the remainder being largely unreacted starting material. The following two examples, 3 and 4, disclose the advantage of the invention by supplying a promoter quantity of t-alkoxide ion.

EXAMPLE 3

A mixture of 337 g (0.983 mole) of 2-bromoethyl-dibromobenzene, 337 g of ar-dibromostyrene contaminated with 2-bromoethyl dibromobenzene, 200 g (2.50 mole) of 50 percent sodium hydroxide solution, 2 g of sodium chloride, 10 ml (7.79 g. 0.105 mole) of t-butanol, and 3 g (0.0119 mole) of triethylpentyl ammonium bromide was stirred 3.5 ks (1 hour) at 5 Hz (300 rpm) at 318 K. (45° C.). The phases were separated after 500 ml of water was added and the organic phase was stirred with fresh sodium hydroxide saturated with sodium chloride, fresh t-butanol, and fresh phase transfer catalyst for an additional 3.6 ks. The yield of product was 438 g. GC analysis showed 0.78 percent ar-bromostyrene, 96.43 percent ar-dibromostyrene, and 2.79 percent ar-tribromostyrene with no starting material present.

When 1.4852 g of the product was diluted with 5 ml of acetone and then 5 ml of methanol, solid polymer precipitated. This was washed with fresh solvent, then dried in a vacuum dessicator at 363 K. (90° C.) for 14 ks (4 hours). The weight of polymer was 0.3155 g (21.24 percent of the product mixture).

EXAMPLE 4

A mixture of 174.6 g (0.509 mole) of 2-bromoethyl-dibromobenzene, 200 g (2.50 mole) of 50 percent sodium hydroxide solution, 2 g of sodium chloride, 10 ml (7.79 g. 0.105 mole) of t-butanol, and 6.5 g (0.0258 mole) of triethylpentyl ammonium bromide was stirred for 7 ks (2 hours) at 5 Hz (300 rpm) at 313 K. (40° C.). GC analysis showed an 87.8 percent conversion of starting material to ar-dibromostyrene. Stirring was continued for another 7 ks and GC analysis showed the conversion to be 98.2 percent. The product was washed with five 500 ml portions of water, dried over calcium sulfate (Drierite), and stirred under a high vacuum (33 Pa or 0.2 torr) for 2 ks (30 minutes). The yield of product was 111.55 g (83.2 percent of theory).

EXAMPLE 5 ar-Dibromostyrene

A solution of sodium ethoxide was prepared by dissolving 52.8 g (2.296 g-at) of sodium metal in 800 ml of absolute ethanol. To this solution was added 624.74 g (1.822 mole) of 2-bromoethyl-dibromobenzene over a period of 1.2 ks (20 minutes). The mixture was stirred under nitrogen for 11 ks (3 hours) at 7 Hz (420 rpm) at 303 K. (30° C.). The product was diluted with 1-1 of water and the phases were separated. The organic phase was washed with two 1-1 portions of water, dried over calcium sulfate (Drierite), vacuum stripped at 33 Pa (0.2 torr) for 1.8 ks (30 minutes), then treated with 5 g of activated carbon (Nuchar-S-A) for 3.6 ks (1 hour) and filtered. 400 ppm of tert-butylcatechol was added as a polymerization inhibitor. The yield of yellow product was 410 g (68.2 percent of theory). GC analysis indicated 0.1 percent ar-bromostyrene, 98.7 percent ar-dibromostyrene, and 1.2 percent ar-tribromostyrene.

Methanol precipitation and gel permeation chromatography both showed less than 0.1 percent polymer in the product.

I claim:
1. A process for the preparation of an ar-dibromostyrene, said process comprising heating a 2-bromoethyl dibromobenzene at a temperature sufficient to remove HBr from said dibromobenzene and form said ar-dibromostyrene; said process being conducted in the presence of an alkaline mixture of
   (i) a promoter quantity of aqueous t-alkoxide ion, and
   (ii) a catalytic quantity of a phase transfer catalyst.

2. The process of claim 1 wherein said temperature is from about 0° C. to about 150° C.

3. The process of claim 1 wherein said temperature is from about 20° C. to about 45° C.

4. The process of claim 1 wherein said phase transfer catalyst is a quaternary ammonium salt.

5. The process of claim 1 wherein said phase transfer catalyst is triethylamyl ammonium bromide.

6. The process of claim 1 wherein said alkoxide ion is t-butoxide.

7. A process for the preparation of ar-dibromostyrene, said process comprising heating 250–450 parts by weight 2-bromoethyl dibromobenzene at about 20° to about 70° C.; said process being conducted in the presence of a mixture of (i) about 100 to about 300 parts 50 percent by weight of sodium hydroxide solution, substantially saturated with sodium chloride, (ii) about 3 to about 10 parts by weight of 2-methyl-2-hydroxypropane, and (iii) about 1 part to about 6 parts by weight of triethylpentyl ammonium bromide.

* * * * *